United States Patent [19]

Leighton

[11] Patent Number: 4,705,854
[45] Date of Patent: Nov. 10, 1987

[54] PHENOTHIAZINE COMPOUNDS

[75] Inventor: Harry J. Leighton, Chapel Hill, N.C.

[73] Assignee: Burroughs Wellcome Co., Research Triangle Park, N.C.

[21] Appl. No.: 738,846

[22] Filed: May 28, 1985

[30] Foreign Application Priority Data

May 31, 1984 [GB] United Kingdom ............... 8413915

[51] Int. Cl.$^4$ ........................................... C07D 279/28
[52] U.S. Cl. ...................................... 544/41; 544/42; 544/43; 544/44; 544/45; 544/46
[58] Field of Search ....................... 544/41, 42, 43, 44, 544/45, 46; 514/79, 80, 85, 86, 89, 90, 91, 92, 93, 94, 223, 224

[56] References Cited

U.S. PATENT DOCUMENTS

| 2,789,978 | 4/1957 | Rath .............................. | 544/41 X |
| 2,941,999 | 6/1960 | Jacob et al. ..................... | 544/41 |
| 2,956,996 | 10/1960 | Craig .............................. | 544/42 X |
| 3,112,310 | 11/1963 | Cusic et al. ...................... | 544/42 X |
| 3,987,042 | 10/1976 | Gueremy et al. ................ | 544/43 |
| 4,451,461 | 5/1984 | Dubroeucq et al. ............. | 544/43 X |
| 4,634,699 | 1/1987 | McDermed et al. ............. | 514/223 |

FOREIGN PATENT DOCUMENTS

| 70753 | 1/1983 | European Pat. Off. |
| 2132194 | 7/1984 | United Kingdom. |

OTHER PUBLICATIONS

Messer et al., Arzneim.-Forsch., vol. 19(8) 1969, pp. 1193-1198.
Barbe et al., Annales Pharm. Francaises, vol. 31(3) 1973, pp. 227-236.
Gritsenko et al., Chemical Abstracts, vol. 76(1972) 3774k.

Primary Examiner—Richard L. Raymond
Attorney, Agent, or Firm—Donald Brown

[57] ABSTRACT

The present invention relates to compounds of the formula (I):

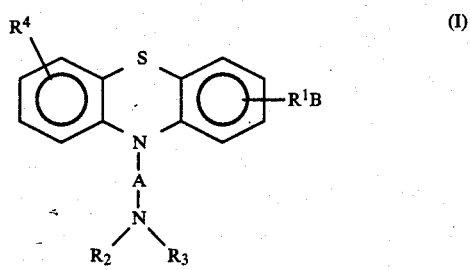

or a salt, ester or amide thereof; wherein $R^1$ is a $C_{1-7}$ bivalent aliphatic hydrocarbon group or a single bond;

$R_2$ and $R_3$ are the same or different and are each hydrogen, $C_{1-4}$ alkyl or taken together with the nitrogen comprise a nitrogen-containing heterocyclic ring having four to six ring members;

$R^4$ is hydrogen, halogen, $C_{1-4}$ alkoxy, $C_{1-4}$ alkyl optionally substituted by one to three halogen atoms; or a group $R_1CO_2H$ as hereinbefore defined; and A is $C_{1-4}$ alkylene or $ANR_2R_3$ forms a group —CH$_2$—(CH$_2$)$_2$ or CH$_2$—(CH$_2$)$_2$ B is an acidic group other than a mono-carboxylic acid group of comparable or greater acid strength than a carboxylic acid group in a similar chemical environment, provided that any sulphonamide group contains at least one N-H bond.

Also disclosed are processes for the preparation of the compounds of the formula (I), chemical intermediates for use in their preparation, and pharmaceutical formulations containing the said compounds.

The compounds have antiallergic activity as defined by blockade of anaphylactoid activity. Certain of the compounds also have good antihistaminic activity.

2 Claims, No Drawings

PHENOTHIAZINE COMPOUNDS

The present invention relates to new chemical compounds exhibiting antihistamine and anti-allergic activity, to processes for preparing them, to novel intermediates involved in thier preparation, to pharmaceutical compositions containing them and to their use in medicine.

U.S. Pat. No. 2,530,451 discloses a group of 9-(dialkylaminoalky)phenothiazines with antihistamine activity, the most outstanding of which is the compound named and hereinafter referred to by its generic name, promethazine (10-(2-dimethylaminopropyl)phenothiazine). Promethazine has gained a fair degree of clinical acceptance as a tranquilliser and as an antihistamine.

The antihistamines now in use, including diphenylhydramine, the pheniramines, pyrilamine, promethazine and triprolidine have one potential disadvantage in common; they all cause sedation or drowsiness in some patients. Promethazine also has the additional disadvantage that it has potent anticholinergic activity.

A novel group of compounds having antiallergic activity in-vivo as defined by blockade of anaphylactoid activity has now been discovered. Some of these compounds also have good antihistamine activity and appear to be substantially free of CNS side-effects and to possess markedly less anticholinergic activity than promethazine.

According this invention provides a compound of the formula (I)

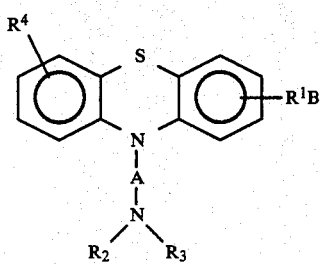

(I)

or a salt, ester or amide thereof; wherein
$R^1$ is a $C_{1-7}$ bivalent aliphatic hydrocarbon group or a single bond;
$R^2$ and $R^3$ are the same or different and are each hydrogen, $C_{1-4}$ alkyl or taken together with the nitrogen comprise a nitrogen-containing heterocyclic ring having four to six ring members;
$R^4$ is hydrogen, halogen, $C_{1-4}$ alkoxy, $C_{1-4}$ alkyl optionally substituted by one to three halogen atoms; or a group $R_1 \, CO_2H$ as hereinbefore defined; and
A is $C_{1-4}$ *alkylene or* $ANR_2R_3$ forms a group

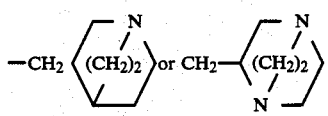

B is an acidic group other than a mono-carboxylic acid group of comparable or greater acid strength than a carboxylic acid group in a similar chemical environment, provided that any sulphonamide group contains at least one N—H bond.

Of the compounds of formula (I) those of formula (II) are preferred;

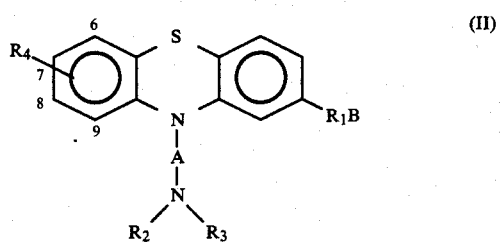

(II)

or a salt, ester or amide thereof; wherein $R_1$ to $R_4$, A and B are as defined in relation to formula (I), and provided that any sulphonamide group contains at least one N—H bond.

$R_1$ may be a straight or branched chain, saturated or unsaturated hydrocarbon group or a single bond. Suitably $R_1$ is a $C_{1-3}$ hydrocarbon group or a single bond. Suitably $R_1$ contains at the most one double bond. Preferably $R_1$ is a group $(CH_2)_n$ wherein n is an integer 0 to 3, or a group CH=CH or a group $—CH(CH_3)(CH_2)_m—$ where m is 0 or 1, or a group $—C(CH_3)_2—$.

Suitably $R_2$ and $R_3$ are the same or different and each is methyl or ethyl or taken together with the nitrogen atom to which they are attached form a four to six membered heterocyclic ring, preferably a saturated heterocyclic ring such as pyrrolidine, piperidine or morpholine. $NR_2R_3$ is most suitably a dimethylamino group, or a diethylamino group, and preferably a dimethylamino group.

Suitably $R_4$ is hydrogen, halogen, $C_{1-4}$ alkyl, or trifluoromethyl. Most suitably $R_4$ is hydrogen, methyl, ethyl, chloro or fluoro. Preferably $R_4$ is hydrogen. When $R_4$ is other than hydrogen it is suitably attached at the 7- or 8-position of the phenothiazine ring system and conveniently at the 7-position.

Suitably A is an ethylene or n- or iso-propylene group or $ANR_2R_3$ forms a group

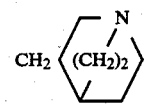

Suitably B is a sulphonic or phosphonic acid group, or an acidic amide thereof, that is to say a group such as $—SO_2NH_2$ containing at least one N—H linkage or a phosphonamide containing an acidic hydroxyl group; or B is a hydroxamic acid group, a dicarboxylic acid group, such as malonic or an optionally substituted five to six membered heterocyclic group that contains an acidic hydrogen atom, such as tetrazole. Preferably B is a tetrazole group, a sulphonic acid group or a phosphonic acid group.

Thus in one preferred aspect of the present invention there is provided a compound of the formula (II):

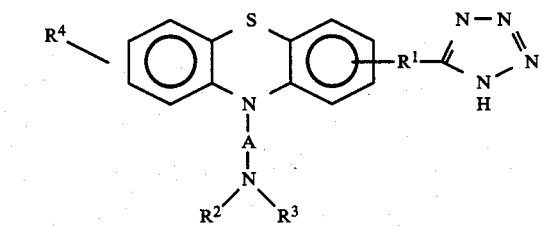

or salt thereof, wherein $R^1$–$R^4$ are as hereinbefore defined.

Particularly preferred compounds of the formula (III) are those wherein $R^1$ is a bond or a group —CMe$_2$—.

In another preferred aspect there is provided a compound of the formula (IV):

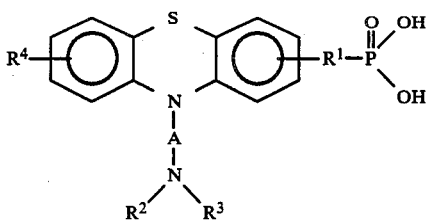

or a salt, ester or amide thereof, wherein $R^1$–$R^4$ are as hereinbefore defined.

In still another preferred aspect there is provided a compound of the formula (V):

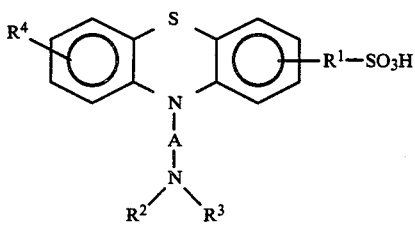

or a salt, ester or acidic amide thereof, wherein $R^1$–$R^4$ are as hereinbefore defined.

The present invention provides in another preferred aspect a compound of the formula (VI):

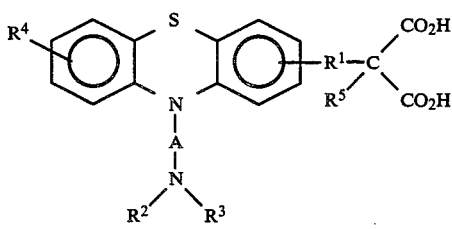

or a salt, amide or ester thereof, wherein $R^1$–$R^4$ are as hereinbefore defined and $R^5$ is hydrogen or $C_{1-4}$ alkyl.

Solvates of the compounds of the formula (I) are also included within the scope of the present invention. Preferred solvates include hydrates and $C_{1-4}$ alkanolates.

Esters and amides of the compounds of the formula (I) whilst having some antihistamine activity in their own right may also be useful intermediates in the preparation of the carboxy compounds of the formula (I). Suitable esters include conventional ester groups known to be useful for protecting carboxylic acid groups such as $C_{1-6}$ alkyl esters wherein the alkyl group is a straight or branched chain and is optionally substituted by halogen. Alkyl esters ($C_{1-4}$) are particularly preferred. Salts of the compounds of formula (I) may be either acid addition salts or salts formed with the acid group. Acid addition salts are preferred but salts formed from the acid group may be particularly useful in preparing the corresponding acidic compound. Pharmaceutically acceptable salts are preferred.

When used in medicine, the salts of the compound of formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable acid additions salts include, but are not limited to, those prepared from the following acids: hydrochloric, sulphuric, nitric, phosphoric, maleic, salicyclic, toluene-p-sulphonic, tartaric, citric, methanesulphonic, formic, malonic, isothionic, succinic, naphthalene-2-sulphonic and benzenesulphonic. Also, pharmaceutically acceptable salts can be prepared as alkaline metal or alkaline earth salts, such as sodium, potassium or calcium salts of the acid group.

When the compounds of formula (I) contain a double bond in the side chain terminating in the acid group, they exist in either the cis or trans isomeric form(s) (in relation to the aromatic ring). Both isomers and the isomeric mixture of these compounds are included within the scope of the present invention. When $R_1$ B contains a double bond, the preferred isomers are those wherein the acid group is trans to the aromatic ring.

Preferred compounds of the formula (I) include:
2-(5-Tetrazolyl)-10-(3'-N,N-dimethylaminopropyl)-phenothiazine,
2-(10-(3-Dimethylaminopropyl)phenothiazine phosphonic acid,
10-(3'-N,N,-Dimethylaminopropyl)phenothiazine-2-sulphonic acid,
2-(2-(5-Tetrazolyl)-prop-2-yl)-10-(3'-N,N-dimethylaminopropyl)phenothiazine,
or salts, esters or acidic amides thereof, The present invention also provides analogy methods of preparing compounds of formula (I), for example:

(a) when it is required to prepare a compound of the formula (I) wherein B is a tetrazolyl or hydroxamic acid group, the conversion of a compound of the formula (I) which is substituted by a group $R^1CO_2H$ to a compound of the formula (I) wherein B is an acid group as hereinbefore defined.

(b) When it is required to prepare a compound of the formula (I) wherein $ANR_2R_3$ is not

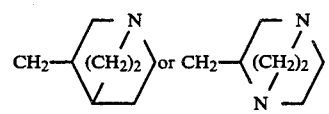

The reaction of a compound of the formula (III):

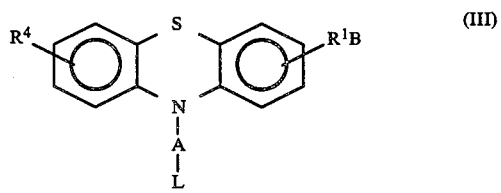

or an ester thereof with an amine $HNR_2R_3$ wherein A and $R_1$ to $R_4$ are as hereinbefore defined and L is a leaving group;

(c) when it is required to prepare a compound of the formula (I) wherein B is a tetrazolyl group (i) the reaction of a compound of the formula (IV):

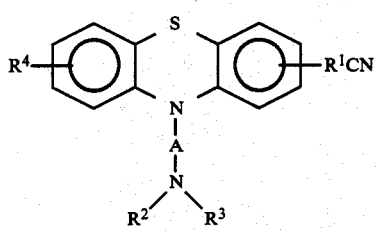

wherein $R^1$ to $R^4$ and A are as hereinbefore defined with hydrazoic acid or a salt thereof:

(d) When it is required to prepare a compound of the formula (I) wherein $R_1$ is $(CH_2)_aCH=CH(CH_2)_b$ and a is 0 and b is 0 to 5 the reaction of a compound of the formula (V):

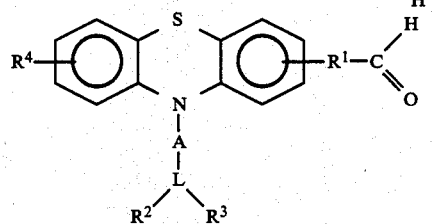

wherein $R^2$, $R^4$ and A are as hereinbefore defined and $R^1$ is a single bond with a Wittig reagent suitable for attaching the side chain $CH=CH(CH_2)_bB$, wherein B is an acid, ester or amide group as hereinbefore defined, followed by deprotection of the acid group if desired;

(e) the alkylation of a compound for the formula (VI):

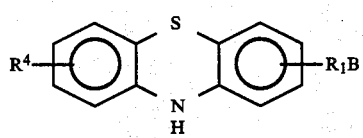

wherein $R_1$ and $R_4$ are as hereinbefore defined, B' is an ester or amide of the group B.

(f) When it is desired to prepare a compound of the formula (I) wherein B contains at least one acidic hydroxyl group, for example when B is a sulphonic, phosphonic, or malonic acid, the hydrolysis of the corresponding ester or amide thereof;

(g) optional conversion of one compound of the formula (I) to another compound of the formula (I).

(a) The preparation of a hydroxamic acid or tetrazolyl compound of the formula (I) from the corresponding compound where the substituent on the X containing ring is $R_1CO_2H$ will be carried out under conventional conditions well known to those skilled in the art. The carboxylic acid group is conveniently converted into an activated derivative, for example an acid anhydride or acid halide, in the first step of this reaction. This will be done under standard conditions, i.e. in an aprotic solvent, such as a halogenated hydrocarbon, an ether or a dipolar aprotic solvent at a non-extreme temperature of between $-50°$ and $100°$ C., preferably at room temperature. The activated acid derivative is then reacted with a substance that will give a compound of the formula (I) or an intermediate for this. A man skilled in the art will know which substances need to be used to give the different acid groups B. For example, the compound of the formula (I) wherein B is tetrazole is prepared by the following reaction scheme.

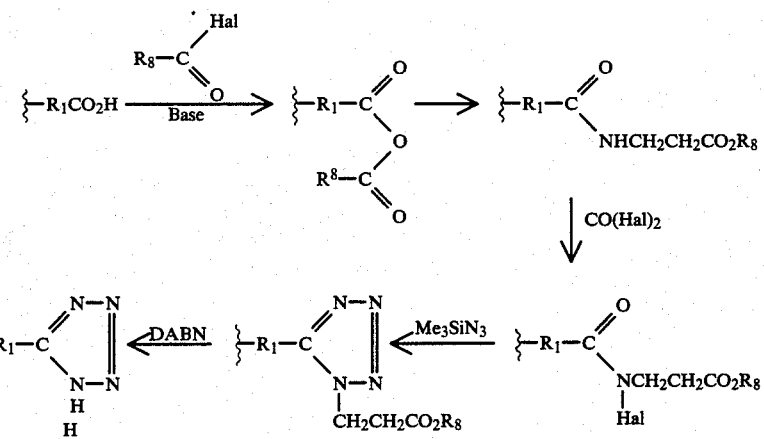

$R_8 = C_{1-6}$ alkyl
Hal = halogen, eg. chlorine

Other heterocyclic acid groups may be prepared in a similar manner. Hydroxamic acid may be prepared as follows.

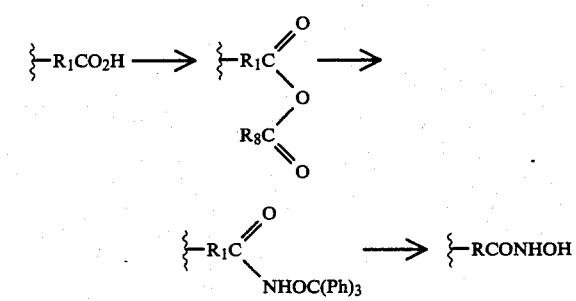

The compounds of the formula (I) wherein the substituent is $R_1CO_2H$ are prepared as described in U.K. Patent Application No. 8332066.

(b) Suitable leaving group L in the compounds of the formula (III) are those as defined by J. March, *Advanced Organic Chemistry*, 2nd ed., pages 683 and 895, McGraw Hill, New York, 1977, e.g. —Br, —Cl, toluenesulphonate, methane sulphonate, acyloxy (such as acetate), etc.

This reaction will normally be carried out in a solvent suitable for carrying out such displacement reactions, for example a polar solvent, such as a $C_{1-4}$ alkanol or a polar aprotic solvent such as DMSO, at a temperature between 0° and 180° C.

The compounds of the formula (III) may be preared by the reaction of the corresponding compound of the formula (III), wherein the acid group B is protected and L is a hydroxy group, with an acid or a suitable reactive acid derivative, followed by deprotection of the acid group if desired. Suitable reactants include hydrogen halides, halogenated phosphorus compounds such as phosphorus pentachloride or phosphorus oxychloride, a suitable sulphonyl chloride (such as methane sulphonyl chloride or p-toluene sulphonyl chloride) or an acid anhydride, such as acetic anhydride. the reaction will conveniently be carried out in a suitable solvent under conditions well known to those skilled in the art, for example in a non-protic solvent such as an ether or a halogenated hydrocarbon, in the presence of a base such as a tertiary amine (for example triethylamine) at a non-extreme temperature, for example between 0° and 100° C. and conveniently at room temperature. when a tertiary amine is used as a base, an excess of this may be used as the solvent.

The hydroxy compounds may be prepared by reacting phenothiazine unsubstituted at the 10-position (i.e. by the group AL) with either alkylene oxides such as ethylene (or higher) oxide, or with an alkanol which also bears a leaving group, in the presence of a strong base, such as an alkali alcoholate, at a non-extreme temperature, for example between 0° and 100° C.

(c) The hydrazoic acid may be either liberated from a suitable source in -situ, for example from an ammonium salt, such as ammonium chloride, and azide ion, for example from sodium azide, or may be added as the free acid. the reaction is normally carried out in a dipolar aprotic solvent, for example dimethylformamide, at a non-extreme temperatue, for example between 0° and 200° C., suitably 50°–150° C. and conveniently at about 100° C.

The compounds of the formula (IV) wherein $R^1$ is a $C_{1-7}$ bivalent alipatic hydrocarbon group may be prepared by the reaction of a compound (V) wherein $R^1$ is a bivalent hydrocarbon group, as hereinbefore defined, with a compound $L^1CH_2NC$ wherein $L^1$ is a sulphonyloxy group, for example tosyl, in the presence of a base, for example an alkali metal alkoxide, such as potassium butoxide, in an aprotic solvent such as dimethyl sulphoxide, at a non-extreme temperature, for example −20° to 100° C. and conveniently 20° C. The compounds of the formula (IV) wherein $R^1$ is a single bond may also be prepared by the alkylation of a compound of the formula (VII)

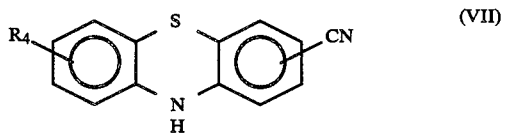

(VII)

under condition substantially similar to those disclosed in UK903725 and as described for process (e) herein. The compound of the formula (VII) may be prepared by the reaction of the corresponding halo-substituted phenothiazine, for example the corresponding chloro-substituted phenothiazine with cuprous cyanide in a base such as N-methylpyrrolidone.

(d) This reaction is a conventional Wittig reaction and, as such, is analogous to those described in Organic Reactions, 14, 270–490 (1965) and Pure and Applied Chemistry, 9, 245–254 (1964). The reaction is suitably carried out in an anhydrous solvent inert under the reaction conditions utilised, for example toluene, benzene, tetrahydrofuran, dioxan, glycol ethers and $C_{1-6}$ alkyl ethers such as ethyl ether, at a temperature between −80° C. and 100° C. the Wittig reagent will normally be prepared by treatment of a phosphonium salt with a strong base, for example a $C_{1-4}$ alkyl or aryl lithium compound such as butyl lithium, or a metal hydride, such as sodium hydride in a suitable inert solvent, such as those specified above.

The Wittig reagent in reaction (d) is conveniently prepared by reacting a compound of the formula $(R_8)_2PO.(CH_2)_dCO_2R_6$, wherein $R_6$ is as hereinbefore defined, $R_8$ is a $C_{1-4}$ alkoxy group and d is 1 to 6, or a compound of the formula $(R_9)_3P(CH_2)_dCH_2R_6$ is as hereinbefore defined $R_9$ is $C_{1-4}$ alkyl or phenyl and d is 1 to 6 with a strong base, such as sodium hydride in a suitable inert solvent, such as tetrahydrofuran or dimethoxyethane at a temperature between 0° and 50° C., conveniently at room temperature.

The reaction between the Wittig reagent and compound of the formula (V) is conveniently carried out by adding the compound of the formula (V) to the Wittig reagent at a temperature of between 0° and 50° C. and conveniently at room temperature.

The compound of formula (V) is suitably prepared by oxidation of the corresponding alcohol under conditions that will not lead to oxidation of the components of the phenothiazine ring, for example by oxidation with silver carbonate on diatomaceous earth in an inert hydrocarbon solvent, such as benzene, at a non-extreme temperature, for example between 0° and 100° C., conveniently under reflux. The alcohol may be prepared by reduction of the corresponding carboxylic acid or its ester, which may be prepared as described in U.K. Patent Application No. 8332060. This reduction may suitably be carried out using a metal hydride, such as lithium aluminium hydride, in an inert solvent, such as an ether, for example diethyl ether, at between 0° and 75° C. and suitably under reflux.

(e) The alkylation of a compound of the formula (VI) is carried out under conditions well known to those skilled in the art of such reactions. The alkylating agent $LANR_2R_3$ (wherein $L,A,R_2$ are as hereinbefore defined), is reacted with the compound of the formula (VI) in the presence of a base at a non-extreme temperature, for example between 0° and 150° C. in an inert solvent.

A strong base is conveniently utilised, for example an alkoxide such as t-butoxide, a hydride such as sodium hydride or sodamide. The temperature is conveniently between 20° and 90° C. and the solvent is suitably a hydrocarbon, such as toluene, an ether, such as tetrahydrofuran, or a dipolar aprotic solvent, such as dimethylformamide or dimethylsulphoxide.

Alternatively a two-phase alkylation system may be employed, which system comprises either solid or aqueous base (e.g. KOH) in a hydrocarbon solvent (e.g. toluene) in the presence of a phase transfer catalyst. When the base is a solid, suitable catalysts are crown-ethers and when aqueous solutions of base are employed, suitable phase transfer catalysts are those such as (n-Bu)₄N⁺HSO₄⁻.

The compounds of the formula (VI) may be prepared by methods well known to those skilled in the art for preparing analogous compounds.

(f) The hydrolysis of amides and esters of the formula (I) can be carried out under conditions well known to those skilled in the art. For example when the group B is a malonic ester, hydrolysis is carried out in the presence of base, for example sodium hydroxide, care being taken to ensure that decarboxylation does not ocur.

The hydrolysis of sulphonamides conveniently is achieved by heating in the presence of a base, for example a sodium alkoxide such as the sodium salt of amyl or isoamyl alcohol. The reaction generally is carried out a polar solvent, such as an alcohol eg. isoamyl alcohol and at moderately high temperatures, for example at around 160° C.

Dialkylamides of sulphonic acids of the formula (I) can be prepared according to standard methods eg. those described in UK 814512.

Thus, for example they can be prepared according to the route shown in the following scheme.

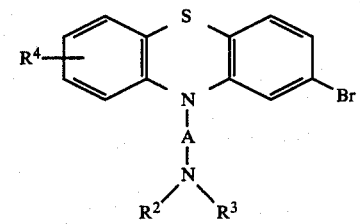

with a phosphorus compound of the formula HP(O)-(OAlk)₂ wherein Alk is a $C_{1-4}$ alkyl group, preferably a t-butyl group. The reaction is conducted in the presence of a palladium catalyst such as $(Ph_3P)_4Pd$ and in the presence of a tertiary amine such as triethylamine.

Compounds of the formula (XIII) can be prepared according to methods analogous to these described in European Patent Application No. 0117302.

(g) The reduction of a double bond, if present in the group $R^1$, may be conveniently be carried out by hydrogenation in the presence of a transition metal catalyst, for example platinum on charcoal. The preparation of

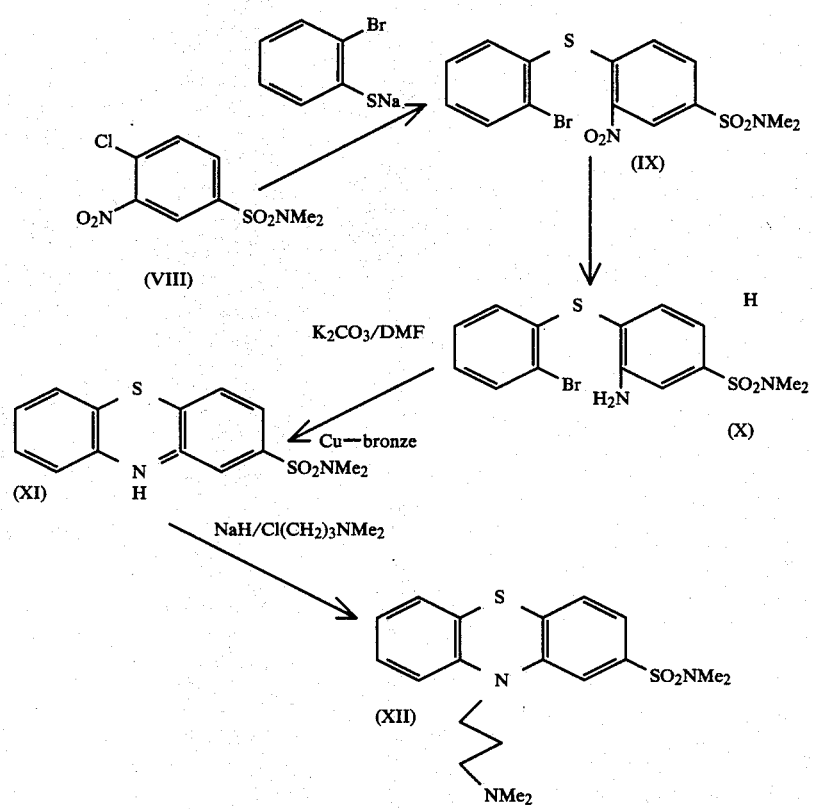

When it is required to hydrolyse an ester of a phosphonic acids of the formula (I), this can conveniently be achieved by treating with acid at a non-extreme temperature. Thus for example such hydrolyses can be conducted in trifluoroacetic acid at approximately ambient temperatures.

Esters of phosphonic acids of the formula (I) can be prepared by reaction of a compound of the formula (XIII):

esters or amides from the corresponding acid, and vice versa, may similarly be carried out by methods well known to those skilled in the art.

Those intermediates that are novel form an important further aspect of the present invention.

The compounds of this invention having antiallergic activity may be used for the same indications as clinically used antiasthmatic compounds, namely to help to control bronchoconstriction or brochospasm characteristic of allergic asthma and exercise induced asthma and the symptoms of bronchoconstriction and bronchospasm resulting from acute or chronic bronchitis. the compounds are believed to inhibit the release of autacoids (i.e. histamine, serotonin and the like) from mast cells and to inhibit directly the antigen-induced production of histamine. Thus, they may be classified as mast cell stabilizers with antihistaminic action.

The compounds of this invention having antihistamine activity may be used for the same indications as clinically used antihistamines, namely to relieve detrimental symptoms (caused by histamine release) of nasal stuffiness due to colds and vasomotor rhinitis and for the symptomatic control of allergic conditions includig nasal allergy, perennial rhinitis, urticaria, angioneurotic oedema, allergic conjunctivitis, food allergy, drug and serum reactions, insect bites and stings and desensitizing reactions. The compound may also be used in conditions responsive to its antipruritic activity including allergic dermatoses, neurodermatitis, anogenital pruritus, and pruritus of non-specific origin such as eczema, and of specific cause such as chickenpox, photosensitivity and sunburn. The present invention therefore provides a method for the symptomatic treatment of allergic conditions by the administration of an effective amount of a compound of the formula (I). The present invention also provides a method for the antagonism of endogenously released histamine by the administration of an effective amount of a compound of the formula (I). Some of the compounds of the present invention have been found to be substantially free from sedative effects and to have little or no anticholinergic effects.

The amount of active compound required for use in the above conditions will vary with the compound chosen, the route of administration and the condition and mammal undergong treatment, and is ultimately at the discretion of the physician. A suitable oral dose of the active compound for a mammal is in the range of from 0.003 to 1.0 mg per kilogram body weight per day; preferably from 0.04 to 0.24 mg/kg. For example a typical dose for a human recipient of compound (B) (see example 2 and Table 1 hereafter) is between 0.03 and 0.1 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.014 to 0.08 mg/kg body weight; for example, a typical sub-dose for such a compound for a human recipient is between 1 and 20 mg, for example 4 or 8 mg.

Whilst it is possible for a compound of the formula (I) to be administered alone as the raw chemical, it is preferable to present the compound of formula (I) as a pharmaceutical formulation. Thus, the present invention also provides pharmaceutical formulations, both for veterinary and for human medical use, which comprise a compound of the formula (I) together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulation include those suitable for oral, rectal, topical, nasal, ophthalmic or parenteral (including subcutaneous, intramuscular and intravenous) administration.

The formulation may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound (defined herein as a compound of formula (I); as a powder or granules; or a suspension in an aqueous liquid or nonaqueous liquid such as a syrup, an elixir, an emulsion or a draught.

A tablet may be made by compression or moulding, optionally with one or more accessory ingredients. Compressed tablets may be prepared by compressing in a suitable machine, with the active compound being in a free-flowing form such as a powder or granules, which is optionally mixed with a binder, disintegrant, lubricant, inert diluent, surface active agent or dispersing agent. Moulded tablets comprised of a mixture of the powdered active compound with any suitable carrier may be made by moulding in a suitable machine.

A syrup may be made by adding the active compound to a cncentrated, aqueous solution of a sugar for example sucrose to which may also be added any accessory ingredient(s). Such accessory ingredient(s) may include flavouring, an agent to retard crystallization of the sugar or an agent to increase the solubility of any other ingredient, such as a polyhydric alcohol, for example glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except that the pH and isotonic factors are adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants surface agents, thickeners, lubricants, preservatives (including antioxidants) and the like.

The present invention also provides the first use of the compounds of the formula (I) in medicine.

The following examples are provided by the way of illustration of the present invention and should in no way be construed as a limitation thereof. All temperatures indicated are in degrees celsius.

EXAMPLE 1

2-(5-Tetrazolyl)-10-(3-N,N-dimethylaminopropyl)-phenothiazine hydrochloride

1A. 2-cyanophenothiazine

A mixture of 2-chlorophenothiazine (70.12 g), copper (I) cyanide (32.24 g) and N-methylpyrrolidinone (150 ml) were heated at reflux for 23 hours. The reaction mixture was then quenched with water (900 ml) and sodium cyanide (29.4 g) added. After heating the mixture to 30°-40° C. the black gummy product was extracted with ethyl acetate (3×250 ml). The combined ethyl acetate layers were then washed with water (2×300 ml); some brine being used to break an emulsion which formed durng each wash. Then, after drying the solution and subsequent rotary evaporation, a brown yellow solid product of crude 2-cyanophenothiazine (51 g) was obtained. This material was purified by heating it at reflux as a solution in ethanol with added activated charcoal. After filtering the hot solution thrugh Hyflo it was rotary evaporated to near dryness which resulted in a slurry of purified yellow product which was filtered off and dried (33.3 g).

1B.
2-Cyano-10-(3-N,N-dimethylaminopropyl)-phenothiazine

The 2-cyanophenothiazine (5 g) of example 1A was dissolved in dimethylformamide (20 ml) and then sodium hydride (0.56 g) as added forming a dark coloured solution. To this solution was then added the 2-N,N-dimethylaminopropylchloride (2.98 g) producing a red coloured solution which was left to stir at room temperature for 18 hours. The reaction mixture was then heated at 70° C. for 2.5 hours, cooled and then quenched with water (250 ml) before being extracted with ethylacetate (2×125 ml). The combined ethylacetate extracts were then extracted with 2N HCl (50 ml). The acid extract was washed with ethyl acetate (4×100 ml), basified with 2N NaOH (50 ml) and the product oil extracted with ethylacetate (3×100 ml). The combined ethylacetate extracts were washed with water, dried and rotary evaporated to give 3.2 g of a black crude solid. This solid was triturated with ether to give 1.24 g of yellow 2-cyano-10-(3-N,N-dimethylaminopropyl)-phenothiazine (Mpt.=82°-84° C. after crystallisation from pet. ether 40/60).

1C.
2-(5-tetrazolyl)-10-(3-N,N-dimethylaminopropyl)-phenothiazine hydrochloride A mixture of 2-cyano-10-(3-N,N-dimethylaminopropyl)phenothiazine (1 g), sodium azide (0.23 g), ammonium chloride (0.21 g) and dimethylformamide (2 ml) was heated at 104° C. for 16 hours. The resultant solution was rotary evaporated to near dryness and the residue mixed with 2N HCl (40 ml) and then the whole rotary evaporated again to near dryness. The residue was triturated with acetone to yield 1.1 g of a powdery orange solid.

The orange solid was crystallised twice from methanol/ether to give 0.17 g of product tetrazole. Mpt.=235°-237° C. (nitrogen evolved at melting point).

Analysis: Calculated for $C_{18}H_{21}ClN_6S.HCl$; C, 55.59; H, 5.44; N, 21.61; Cl, 9.12. Found; 55.35; H, 5.42; N, 21.25; Cl, 9.05.

EXAMPLE 2

2-N,N-Dimethylsulphamoyl-10-(3-N,N-dimethylaminopropyl)phenothiazine oxalate

2A.
2-Bromo-2'-nitro-4'-N,N-dimethylsulphamoyl-biphenyl thioether

To N,N-dimethyl-4-chloro-3-nitrobenzenesulphonamide (28 g) in ethanol (210 ml) was added an ethanolic solution of sodium 2-bromophenylthiolate (2-bromo thiophenol (20 g), sodium hydroxide (4.4 g), water (9 ml) and ethanol (100 ml). The whole then refluxed gently for 20 hours, before most of the ethanol was removed under vacuum leaving a yellow paste. The solid was filtered, washed with ethanol then water and finally with ethanol. The product was dried in a vacuum oven at 60° C., 42.15 g, 95% yield mpt.=142°-144° C.

2B.
2-Bromo-2'-amino-4'-N,N-dimethylsulphamoyl-biphenyl thioether

The nitro compound (2A) (20 g), iron powder (9.37 g), acetic acid (19.3 ml) and ethanol (120 ml) were heated at reflux for 3.25 hours. After cooling the reaction mixture it was poured into water (600 ml) and the iron-contaminated solid filtered off, and washed with water. The solid was then dissolved in SVM and filtered through Hyflo. The SVM was then removed under vacuum giving after drying an off-white solid (15.5 g) 84%. mpt.=140°-142° C.

2C. 2-(N,N-Dimethylsulphamoyl)-10-H-phenothiazine

The bromoaniline (2B) (15 g) was mixed with copper bronze (2.48 g) and potassium carbonate (5.9 g) in dimethylformamide (50 ml) and the whole heated at reflux for 2 hours. The reaction mixture was cooled and poured into water (300 ml) and the product extracted with ethylacetate (2×150 ml). The ethyl acetate extracts were washed with water, dried over magnesium sulphate and finally the ethyl acetate was removed under vacuum to give a brown solid (11.7 g) 99% crude yield. The crude material was purified with an ethanol charcoal treatment giving 4 g of a yellow powdery solid of the phenothiazine (C). mpt.=175°-177° C.

2D.
10-(3'-N,N-Dimethylaminopropyl)-2-(N,N-dimethylsulphamoyl)-10-H-phenothiazine The alkylated title phenothiazine was prepared by standard alkylation of (2C) using $NaH/DMF/Cl(CH_2)_3NMe_2$ at 70° C., and isolated as the oxalate salt. m.pt.=201°-203° C.

2E.
10-(3'-N,N-Dimethylaminopropyl)phenothiazine-2-sulphonic acid hemihydrate To a solution of sodium (14.3 g) in isoamyl alcohol (150 ml) was added the sulphonamide (2D) (7.83 g) and the whole was then heated with stirring at 160° C. for 7 hours. The reaction mixture was then cooled and 15% hydrochloric acid (140 ml) was added. The reaction liquors were then removed under vacuum leaving a solid residue. To this residue was added water (150 ml) and 2N sodium hydroxide until a pH of 7 was achieved. The aqueous solution was then washed with chloroform and finally the water was removed under vacuum. The product sulphonic acid was extracted from the residue with ethanol. The crude product obtained from the ethanol extraction was then crystallised twice from methanol with charcoal to give 0.83 g. mpt=206°–207° C. as the hemihydrate after drying.

EXAMPLE 3

2-[10-(3-Dimethylaminopropyl)]phenothiazine phosphonic acid

3A.

2-bromo-10-(3'-N,N-dimethylaminopropyl)phenothiazine 2,5-Dibromonitrobenzene (84.27 g) in ethanol (600 ml) was added to a solution of 2-bromo sodium thiophenolate (63.3 g) in ethanol (300 ml). The reaction mixture was heated at reflux for 17 hours and then the solvent removed under vacuum. The solid yellow product was then filtered off and dried m.pt.=85°–86° C., 106.8 g. 2-Bromo-4'-bromo-2'-nitrobiphenyl thioether (50 g) was mixed with iron powder (25.2 g) and glacial acetic acid (52 ml). The whole was then heated at reflux for 23 hours. The reaction mixture was cooled and quenched with water (100 ml). The product was then extracted with ethyl acetate (3×300 ml). The combined ethyl acetate extract were washed with water, then brine and finally dried over MgSO$_4$ before removal of the solvent. The crude material was then crystallised from isopropanol to give 50% of pure 2-bromo-4'-bromo-2'-aminobiphenylthioether mpt.=75° C.

The aminocompound 42 g, copper bronze (7.43 g) and potassium carbonate (17.7 g) in DMF (150 ml) were heated at reflux for 3.25 hours. The reaction mixture was cooled to just above room-temperature and then poured into water (1 liter). The product was then extracted with ethylacetate (4×250 ml), and the combined extracts filtered through Hyflo. The ethyl acetate layer was then washed with water, dried and the solvent removed under vacuum. The residue was then crystallised from benzene to give 2-bromophenothiazine (17 g), mpt.=198°–199° C.

2-Bromophenothiazine was alkylated as usual with 3-N,N-dimethylaminopropylchloride to give the title phenothiazine.

3B. 2-[10-(3-Dimethylaminopropyl)]phenothiazine phosphonic acid

2-Bromo-10-(3-N,N-dimethylaminopropyl)phenothiazine (2.1 g), di-t-butylphosphite (Ref. T. M. Chapman and O. G. Kleid, *J. Organic Chemistry*, 1973, 38, 250) (2.93 g), triethylamine (0.88 ml), palladium tetrakistriphenylphosphine (0.34 g) and toluene were mixed and heated with stirring at ca. 95° C. under nitrogen for 16 hours. At this stage reaction was incomplete as judged by TLC so an extra aliquot of triethylamine (0.81 ml) and palladium catalyst (0.6 g) was added and reaction continued for 24 hours. The reaction mixture was then poured into 2N HCl (70 ml), and this aqueous layer washed with ether. The aqueous layer was then basified with 2N NaOH and the product extracted with ether. The combined ether layers were then washed with water, dried and the ether removed under vacuum to give the crude product di-t-butyl-phosphonate phenothiazine which was impregnated on dry column silica (30 g) and eluted through a silica column to give 0.9 g of pure di-t-butylphosphonate phenothiazine.

The di-t-butylphosphonate phenothiazine (0.9 g) was then mixed with trifluoroacetic acid (10 ml) and stirred at room-temperature for 22 hours. The trifluoroacetic acid was then removed under vacuum and the residue treated with 2N NaOH (6 ml) and water (3 ml). The resultant yellow solution was washed with ether then acidified to pH 1 whereupon a dark viscous oil precipitated. The aqueous layer was decanted off. The residue was then extracted with methanol (5 ml) then precipitated with ether (50 ml). The tacky solid precipitate was then triturated with acetone to give a brick red powdery solid (0.36 g). The brick-red solid was crystallised from methanol to give (0.17 g) of the title phosphonic acid phenothiazine mpt.=268°–269° C.

EXAMPLE 4

4A. 2-Methyl-2-(4-bromophenyl)propionitrile

To a suspension of sodium hydride (60% dispersion in oil, 50 g, 1.25 m) in dry N,N-dimethylformamide (400 ml under nitrogen was added with stirring a solution of 4-bromophenylacetonitrile in N,N-dimethylformamide (400 ml) keeping the temperature between 30° and 40° C. A solution of iodomethane (213 g, 1.50 m) in N,N-dimethylformamide was then added gradually keeping the temperatue between 35° C. and the mixture then stirred at ambient temperature overnight. With ice cooling 2N aqueous hydrochloric acid (800 ml) was gradually added and then the mixture was diluted with water (1200 ml). The product was extracted with ether and the extract washed with water, saturated sodium bicarbonate, aqueous sodium sulphite, water again and finally brine. After drying and concentration on vacuo an orange oil was obtained which was distilled in vacuo to give the title compound as a colourless liquid (98.05 g, 87.5%) b.pt. 98°–100°/0.4 mm.

4B. 2-Methyl-2-(3-nitro-4-bromophenyl)propionitrile

Concentrated sulphuric acid (80 ml) was added slowly to concentrated nitric acid (80 ml) with stirring and ice cooling. The previous product (77 g, 0.344 m) was then added dropwise with cooling to maintain the temperature below 55° C. The yellow solution was then carefully heated to 85° C. and then allowed to cool at room temperature. The mixture was then poured onto crushed ice and the resultant solid was filtered off, washed with water and dried in vacuo over calcium chloride. The crude product was then dissolved in boiling methanol (300 ml) and the solution allowed to cool to give the title compound in the form of yellow crystals (52.06 g, 56%) mpt. 87°–88° C. Calcd for $C_{10}H_9BrO_2$: C, 44.6: H, 3.4; N, 10.4; Br, 29.7; found: C, 44.6; H, 3.3; N, 10.2; Br, 29.8

4C.

2-Methyl-2-(4-phenylthio-3-nitrophenyl)propionitrile

A mixture of thiophenol (9.09 g 0.0826 m), 2-methyl-2-(3-nitro-4-bromophenyl)propionitrile (18.68 g, 0.0694 m), sodium carbonate (16.0 g, 0.151 m) and absolute ethanol (300 ml) was stirred and heated at reflux for 5 hours. The cooled mixture was then poured onto icewater and the resultant yellow solid filtered off. The crude solid was slurried with water/SVM (1.1, 300 ml) and the solid filtered and mixed with water/SVM (1:1, 150 ml. The solid was crystallised from methanol to give yellow needles (14.78 g, 65%) mpt. 146°-147° C. Calcd., for $C_{16}H_{14}N_2SO_2$: C, 64.4 H, 4.7 N, 9.4; S, 10.7 Found: C, 64.5; H, 4.6; N, 9.3; S, 10.8

4D. 2-Methyl-2-(phenothiazin-2-yl)propionitrile

A mixture of the above product (15.0 g, 0.0503 m), triethyl phosphite (33.3 g, 0.201 m) and N-propylbenzene (150 ml) was heated at reflux under nitrogen for 10 hours. The solvent was then removed in vacuo and the dark coloured residue was applied to a column of silica-gel and the column eluted with benzene. Removal of the solvent from the appropriate fractions gave a pale brown solid which was crystallised from ethanol to give the title compound (5.54 g, 44%) as tan crystals mpt. 113°-114° C. Calcd. for $C_{16}H_{14}N_2S$:C, 72.2; H, 5.3; N, 10.5; S, 12.0 Found: C, 72.4; H, 5.4; N, 10.5; S, 12.6

4E. 2-Methyl-2-[10-(3-N,N-dimethylaminopropyl)phenothiazin-2-yl)propionitrile A mixture of the previous product (1.335 g,0.005 m), potassium t-butoxide (0.616 g, 0.0055 m) and N,N-dimethylformamide (20 ml) was stirred together at ambient temperature under nitrogen for 1 hour. To this mixture was then added N,N-dimethyl-3-chloropropylamine (0.616 g, 0.0055 m) and the mixture then heated to 65°-70° C. for 4 hours. After cooling, the solution was poured into ice-water and the product was extracted with ethyl acetate. The dried extract was concentrated in vacuo to give a red gum which was purified by column chromatography on silica gel. The column was eluted with methanol and the appropriate fractions were concentrated in vacuo to give the title compound as a viscous gum (1.53 g, 87%).

4F. 5-[1-[10-(3-N,N-Dimethylaminopropyl)phenothiazine-2-yl]-1-methyl]-ethyl-1H-tetrazole A mixture of the previous product (1.53 g, 0.00427 m), sodium azide (0.30 g, 0.00469 m), ammonium chloride (0.25 g, 0.00469 m) and N,N-dimethylformamide (2.5 ml) were heated with stirring at 130° C. for 18 hours. The mixture was then poured into ice-water and the organic material extracted with chloroform. The dried extract was concentrated in vacuo to give a dark semi-solid which was purified by column chromatography on silica-gel. Elution with methanol and concentration of the appropriate fractions gave a foam which was dissolved in acetone. A slight excess of ethereal hydrogen chloride was added and the mixture further diluted with ether to give a white solid. This solid was then crystallised from methanol/ether to give the hydrochloride of the title compound as white needles mpt. 184°-185° C. calcd. for $C_{21}H_{26}N_6S.HCl$: C, 58.5; H, 6.3; N, 19.5; S, 7.4; Cl, 8.2 Found: C, 58.5; H, 6.2; N, 19.3; S, 7.6; Cl, 8.3

EXAMPLE 5

5A. 2-Methyl-2-[10-(2-N,N-dimethylamino-2-methylethyl)-phenothiazin-2-yl]propionitrile A mixture of 2-methyl-2-(phenothiazin-2-yl)propionitrile (2.90 g, 0.0109 m), potassium t-butoxide (2.44 g, 0.0218 m) and N,N-dimethylformamide (50 ml) was stirred together at ambient temperature for 1 hour. To this mixture was then added 2-chloro-N,N-dimethylaminopropylamine (2.65 g, 0.0178 m) and the mixture was stirred at ambient temperature for 24 hours. A further quantity (2.0 g) of the amine was then added and the mixture stirred and heated at 65°-75° for a further 48 hours. After cooling the solution was poured into ice-water and the product extracted with ethyl acetate. The dried extract was concentrated in vacuo and the crude product which consisted of a mixture of two isomers and some starting material was purified by column chromatography on silica-gel, Elution with methanol gave the major isomer as a viscous gum (1.93 g 50%) after concentration of the appropriate fractions. That this major isomer was the title compound was confirmed by n.m.r. by comparison with the minor-isomer (which has a (2-N,N-dimethylamino-1-methyl)ethyl substituent).

5B. 5-[1-[10 -(2-N,N-Dimethylamino-2-methyl ethyl)phenothiazin-2-yl]-1-methyl]ethyl-1H-tetrazole A mixture of the previous compound (major isomer, 1.93 g, 0.00549 m), sodium azide (0.54 g, 0.00824 m), ammonium chloride (0.44 g, 0.00824 m) and N,N-dimethylformamide (5 ml) was stirred and heated at 13° C. for 23 hours and then at 150° C. for 2 hours. The cooled mixture was then poured onto ice-water and the products extracted with chloroform. The dried extract was concentrated in vacuo to give a brown foam which was purified by chromatography on silica-gel. Elution with methanol and concentration of the appropriate fractions gave a cream coloured foam. This was dissolved in acetone and a slight excess of ethereal hydrogen chloride was added, and the mixture further diluted with ether to give a white solid. This was then crystallised from methanol/ether to give the hydrochloride of the title compound as white crystals mpt. 162-°163° C.

EXAMPLE 6

6A. 2-Methyl-2[4-(4-chlorophenylthio)-3-nitrophenyl]propionitrile

A mixture of 4-chlorothiophenol (6.5 g, 0.045 m), 2-methyl-2-(3-nitro-4-bromophenyl)propionitrile (11.0 g, 0.041 m), sodium carbonate (8.67 g, 0.082 m) and absolute ethanol (150 ml) as stirred and heated at reflux for 4 hours. The mixture was cooled and poured into ice-water and the resultant yellow solid was filtered off. This solid was then slurried in a mixture of water and SVM (1:1, 150 ml) and refiltered and washed with water/SVM (1:1, 150 ml). The solid was crystallised from ethanol to give yellow crystals (11.86 g, 87%) mpt. 159°-160°.

6B. 2-Methyl-2-(7-chlorophenothiazin-2-yl)propionitrile

A mixture of the previous compound (11.42 g, 0.0343 m), triethyl phosphite (22.8 g, 0.137 m) and n-propylbenzene (115 ml) was heated at reflux under nitrogen for 4 hours. The solvent was then removed in vacuo and the residual dark coloured oil was purified by chromatography on silica-gel. Elution with benzene and concentration of the appropriate fractions gave a tan coloured solid which was crystallised from ethanol to give a mustard coloured solid (2.87 g, 28%) mpt. 153°-154° C.

6C.
2-Methyl-2-[10-(3-N,N-dimethylaminopropyl)-7-chlorophenothiazin-2-yl]propionitrile A mixture of the previous compound (2.70 g, 0.0090 m), potassium t-butoxide (1.12 g, 0.0099 m) and N,N-dimethyl formamide (35 ml) were stirred at ambient temperature under nitrogen for 1 hour. To this mixture was then added N,N-dimethyl-3-chloropropylamine (1.64 g, 0.0135 m) and the mixture stirred for one hour and then heated at 75° for 3 hours. The cooled mixture was then poured onto ice-water and the product extracted with ethyl acetate. The dried extract was concentrated in vacuo to give a dark coloured oil which was purified by chromatography on silica-gel. Elution with methanol and concentration of the appropriate fractions gave the title compound as a viscous gum (2.5 g, 72%)

6D.
5-[1-[10-(3-Dimethylaminopropyl)-7-chlorophenothiazin-2-yl)-1-methyl]ethyl-1H-tetrazole A mixture of the previous product (2.50 g, 0.0065 m), sodium azide (0.63 g, 0.0097 m), ammonium chloride (0.52 g, 0.0097 m) and N,N-dimethylformamide (15 ml) were heated together at reflux for 7 hours. A further quantity of sodium azide and ammonium chloride (0.5 eq.) was added and heating continued for a further 3 hours. After cooling, the mixture was poured onto ice-water and the products extracted with chloroform. The dried extract was concentrated in vacuo to give a brown oil which was purified by chromatography on silica gel. Elution with methanol and concentration of the appropriate fractions gave a gum which was dissolved in acetone and then a slight excess of ethereal hydrogen chloride added. The solution was concentrated in vacuo and the residue taken up in methanol and diluted with ether to give a white powder on cooling. This solid was crystallised from methanol/ether to give the hydrochloride of the title compound mpt 183°–184°.

EXAMPLE 7

Antihistamine Activity

A. In vitro antihistamine activity: The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-l) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration response curve 2X to the right.

| Compound of Example No. | $pA_2$ |
|---|---|
| 2. | 7.8 |

EXAMPLE 8

Formulations

| (A)-Injection | |
|---|---|
| Ingredient | Amount per ampoule |
| Compound of formula (I) | 1.0 mg |
| Water for Injections, q.s. | 1.0 mL |

The finely ground active compound was dissolved in the water for Injections. The solution was filtered and sterilized by autoclaving.

| (B)-Suppository | |
|---|---|
| Ingredient | Amount per suppository |
| Compound of Formula (I) | 1.0 mg |
| Cocoa Butter, or Wecobee ™ Base q.s. | 2.0 g |

Wecobee is a trademark and is a hydrogenated fatty carboxylic acid.

The finely ground active compound was mixed with the melted suppository base (either Cocoa Butter or Wecobee ™ base), poured into moulds and allowed to cool to afford the desired suppositories.

| (C)-Syrup | |
|---|---|
| Ingredient | Amount Per mL |
| Compound of formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | q.s. to 5.0 mL |

Ethanol, sucrose, sodium benzoate, methylparaben, and flavouring were combined in 70% of the total batch quantity of water. Colouring and the active compound were dissolved in the remaining water, then the two solutions were mixed and clarified by filtration.

| (D)-Tablet | |
|---|---|
| Ingredient | Amount per Tablet |
| Compound of Formula (I) | 1.0 mg |
| Lactose | 110.0 mg |
| Cornstarch, Pregelatinized | 2.5 mg |
| Potato Starch | 12.0 mg |
| Magnesium stearate | 0.5 mg |

The active compound was finely ground and intimately mixed with the powdered excipients lactose, corn starch, potato starch and magnesium stearate. the formulation was then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |

| (E)-Capsule | |
| --- | --- |
| Ingredient | Amount per Capsule |
| Magnesium Stearate | 5.0 mg |

The finely ground active compound was mixed with the powdered excipients lactose, corn starch and stearic acid and packed into gelatin capsules.

| (F)-Tablet | |
| --- | --- |
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 11 (D).

| (G)-Syrup | |
| --- | --- |
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavour | q.s. |
| Colour | q.s. |
| Glycerol | 500 mg |
| Sucrose | 2000 mg |
| Purified Water | q.s. to 5.0 ml |

A syrup containing other active ingredients in addition to a compound of formula (I) was prepared from the above ingredients by an analogous method to that described for Example 8(C) above.

| (H)-Nasal Spray | |
| --- | --- |
| Ingredient | Amount per 100.0 mL |
| Compound of formula (I) | 1 g |
| Sodium Chloride | 0.8 g |
| Preservative | 0.5 g |
| Purified Water | q.s. 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic Solution | |
| --- | --- |
| Ingredient | Amount per 100.0 mL |
| Compound of Formula (I) | 0.1 g |
| Sodium Chloride | 0.8 g |
| Preservative | 0.5 g |
| Water for Injection | q.s. 100.0 mL |

This formulation was prepared in a similar way to the nasal spray.

| (J)-Topical Cream | |
| --- | --- |
| Ingredient | Amount per 100.0 mL |
| Compound of Formula (I) | 0.1 g |
| Emulsifying Wax, N.F. | 15.0 g |
| Mineral Oil | 5.0 g |

I claim:
1. A compound of formula (III):

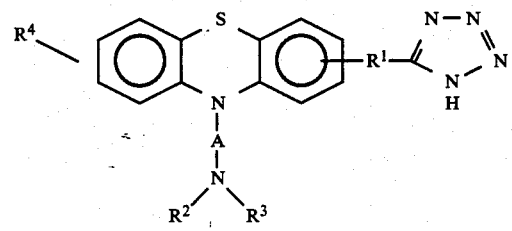

wherein
$R^1$ is a $C_{1-7}$ bivalent aliphatic hydrocarbon group or a single bond;
$R_2$ and $R_3$ are the same or different and are each hydrogen, $C_{1-4}$ alkyl or taken together with the nitrogen comprise a nitrogen-containing heterocyclic ring having four to six ring members;
$R^4$ is hydrogen, halogen, $C_{1-4}$ alkoxy, $C_{1-4}$ alkyl, $C_{1-4}$ alkyl substituted by one to three halogen atoms; or a group $R_1CO_2H$ wherein $R^1$ is herein defined; and
A is $C_{1-4}$ alkylene or $ANR_2R_3$ forms a group

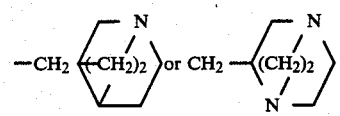

2. A compound of the formula:

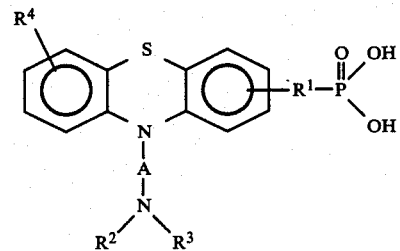

or a salt, ester or amide thereof; wherein
$R^1$ is a $C_{1-7}$ bivalent aliphatic hydrocarbon group or a single bond;
$R_2$ and $R_3$ are the same or different and are each hydrogen, $C_{1-4}$ alkyl or taken together with the nitrogen comprise a nitrogen-containing heterocyclic ring having four to six ring members;
$R_4$ is hydrogen, halogen, $C_{1-4}$ alkoxy, $C_{1-4}$ alkyl, $C_{1-4}$ alkyl substituted by one to three halogen atoms; or a group $R_1CO_2H$ where $R^1$ is herein defined; and
A is $C_{1-4}$ alkylene or $ANR_2R_3$ forms a group

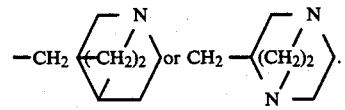

* * * * *